United States Patent
Lizardi et al.

(10) Patent No.: US 7,166,116 B2
(45) Date of Patent: Jan. 23, 2007

(54) TISSUE GRASPER/SUTURE PASSER INSTRUMENT

(75) Inventors: Jose E. Lizardi, Franklin, MA (US); Daniel A. Perkins, Hyde Park, UT (US)

(73) Assignee: Ethicon, Inc., Someriville, NJ (US)

( * ) Notice: Subject to any disclaimer, the term of this patent is extended or adjusted under 35 U.S.C. 154(b) by 476 days.

(21) Appl. No.: 10/601,479

(22) Filed: Jun. 23, 2003

(65) Prior Publication Data
US 2004/0260314 A1 Dec. 23, 2004

(51) Int. Cl.
*A61B 17/06* (2006.01)
(52) U.S. Cl. ...................................... 606/144
(58) Field of Classification Search .............. 606/139, 606/144, 145, 147, 150, 148
See application file for complete search history.

(56) References Cited

U.S. PATENT DOCUMENTS 3,842,840 A * 10/1974 Schweizer ................. 606/145
5,147,373 A   9/1992 Ferzli
5,674,230 A * 10/1997 Tovey et al. ............... 606/139
6,533,795 B1   3/2003 Tran et al.
2002/0173800 A1  11/2002 Dreyfuss et al.
2003/0083695 A1   5/2003 Morris et al.

OTHER PUBLICATIONS

Partial European Search Report EP 04 25 3756 dated Oct. 15, 2004.

* cited by examiner

*Primary Examiner*—Eduardo C. Robert
*Assistant Examiner*—Richard Shaffer
(74) *Attorney, Agent, or Firm*—Emil Richard Skula

(57) ABSTRACT

A needle passer instrument for use in minimally invasive surgical procedures, including arthroscopy. The instrument has upper and lower jaws for engaging tissue and a handle. A removable needle engaging cartridge is mounted to the upper jaw. A surgical needle with attached suture is mounted in a needle passage in the lower jaw. A needle actuation rod engages the surgical needle and pushes the needle through tissue contained between the jaws. The needle is engaged by the cartridge, and the needle may be cut away from the suture.

10 Claims, 20 Drawing Sheets

TISSUE GRASPER/SUTURE PASSER INSTRUMENT

TECHNICAL FIELD

The field of art to which this invention relates is surgical instruments, in particular, surgical instruments for use in minimally invasive surgical procedures.

BACKGROUND OF THE INVENTION

Minimally invasive surgical procedures have proven to be of significant benefit to patients. Typically, in a minimally invasive procedure, a surgical site is accessed using a small incision through a patient's skin and underlying fascia. A conventional trocar cannula may be inserted through the incision to provide a passageway for instruments, scopes, etc. The surgeon may view the operative site remotely or by direct visualization. Many instruments have been developed for minimally invasive surgical procedures including endoscopic and arthroscopic instruments. Arthroscopic instruments that are known and used include, for example, conventional arthroscopic scissors, arthroscopic fastener appliers, and arthroscopic suture passers.

Of particular importance in this art are instruments and methods for applying surgical sutures in an arthroscopic procedure. In an open procedure, the surgeon typically holds a surgical needle in a needle grasper and pushes and pulls the surgical needle through tissue around a tissue site and releases and re-grasps the needle each time the needle is exits the tissue that is required to be approximated. This type of open suturing technique is difficult to perform successfully in an arthroscopic procedure because of the limited working space. Specially designed arthroscopic suture devices have been developed to remotely pass sutures through tissue in arthroscopic procedures.

Although the arthroscopic suture passers of the prior art are adequate for their intended purpose, there is a constant need in this art for new instruments having advantageous characteristics and features that are easy to use in an arthroscopic surgical procedure.

SUMMARY OF THE INVENTION

Therefore, it is an object of the present invention to provide novel surgical instruments for arthroscopic surgical instruments that advantageously pass suture in arthroscopic surgical procedures.

Accordingly, a novel suture passer instrument is disclosed. The suture passer instrument has a frame having a proximal end and a distal end. The frame has a longitudinal passage. A bottom jaw member is mounted to the distal end of the frame. The bottom jaw member has a top surface and a bottom surface. There is a needle passageway in the bottom jaw member having a distal opening out through the top surface of the bottom jaw and a proximal opening in communication with the longitudinal passage of the frame. A top jaw member is pivotally mounted to the distal end of the frame such that the top jaw member is moveable with respect to the bottom jaw member. The top jaw member having a distal opening for receiving a cartridge member. A handle member is mounted to the proximal end of the frame. The handle member has a cavity. There is a jaw actuation member having a top end and a bottom end, wherein the top end of the jaw actuation member is mounted to the handle member. There is also a needle rod driving trigger member having a top and a bottom, wherein the top of the needle rod driving member is pivotally mounted to the handle member. A jaw actuation rod having a proximal end a distal end is slidably mounted in the passage of the frame. The distal end of the jaw actuation rod operably engages the top jaw member, and the proximal end of the actuation rod is mounted to the jaw actuation member. A needle driving rod is slidably mounted to the frame. The needle driving member has a proximal end mounted to the needle driving trigger and a distal end for engaging a surgical needle mounted in the needle passageway.

Yet another aspect of the present invention is a suture passer instrument. The suture passer instrument has a frame having a proximal end and a distal end. The frame has a longitudinal passage. A bottom jaw member is mounted to the distal end of the frame. The bottom jaw member has a top surface and a bottom surface. There is a needle passageway in the bottom jaw member having a distal opening out through the top surface of the bottom jaw and a proximal opening in communication with the longitudinal passage of the frame. A top jaw member is pivotally mounted to the distal end of the frame such that the top jaw member is moveable with respect to the bottom jaw member. The top jaw member having a distal opening for receiving a cartridge member. A handle member is mounted to the proximal end of the frame. The handle member has a cavity. There is a jaw actuation member having a top end and a bottom end, wherein the top end of the jaw actuation member is mounted to the handle member. There is also a needle rod driving trigger member having a top and a bottom, wherein the top of the needle rod driving member is pivotally mounted to the handle member. A jaw actuation rod having a proximal end a distal end is slidably mounted in the passage of the frame. The distal end of the jaw actuation rod operably engages the top jaw member, and the proximal end of the actuation rod is mounted to the jaw actuation member. A needle driving rod is slidably mounted to the frame. The needle driving member has a proximal end mounted to the needle driving trigger and a distal end for engaging a surgical needle mounted in the needle passageway. The instrument has a removable cartridge member mounted in the opening of the top jaw member. The cartridge member has a cavity for receiving and engaging at least part of a surgical needle.

Yet another aspect of the present invention is a method of using the above-described suture passer instruments of the present invention in a surgical procedure to pass a surgical needle and attached suture through tissue.

These and other aspects and advantages of the present invention will become more apparent from the following description and accompanying drawings.

DETAILED DESCRIPTION OF THE INVENTION

The tissue grasper and suture passer instruments of the present invention are preferably used in minimally invasive arthroscopic surgical procedures. However, these instruments may be use in other types of minimally invasive procedures including endoscopic surgical procedures, laparoscopic surgical procedures, etc. The instruments may also be used in open surgical procedures. The tissue grasper and suture passer instruments may be constructed of conventional, biocompatible materials that are easily cleaned and capable of being sterilized. The materials include but are not limited to surgical stainless steel, nitinol, titanium, polycarbonate and the like, and combinations thereof. The cartridges used in the tissue grasper and needle passer instruments of the present invention are preferably made from conventional biocompatible polymeric materials that are readily sterilizable including but not limited to polyethylene, polycarbonate, ABS and the like. The cartridges may also be made from the previously-mentioned metals, and combinations of metals and polymeric materials.

Figure 1:
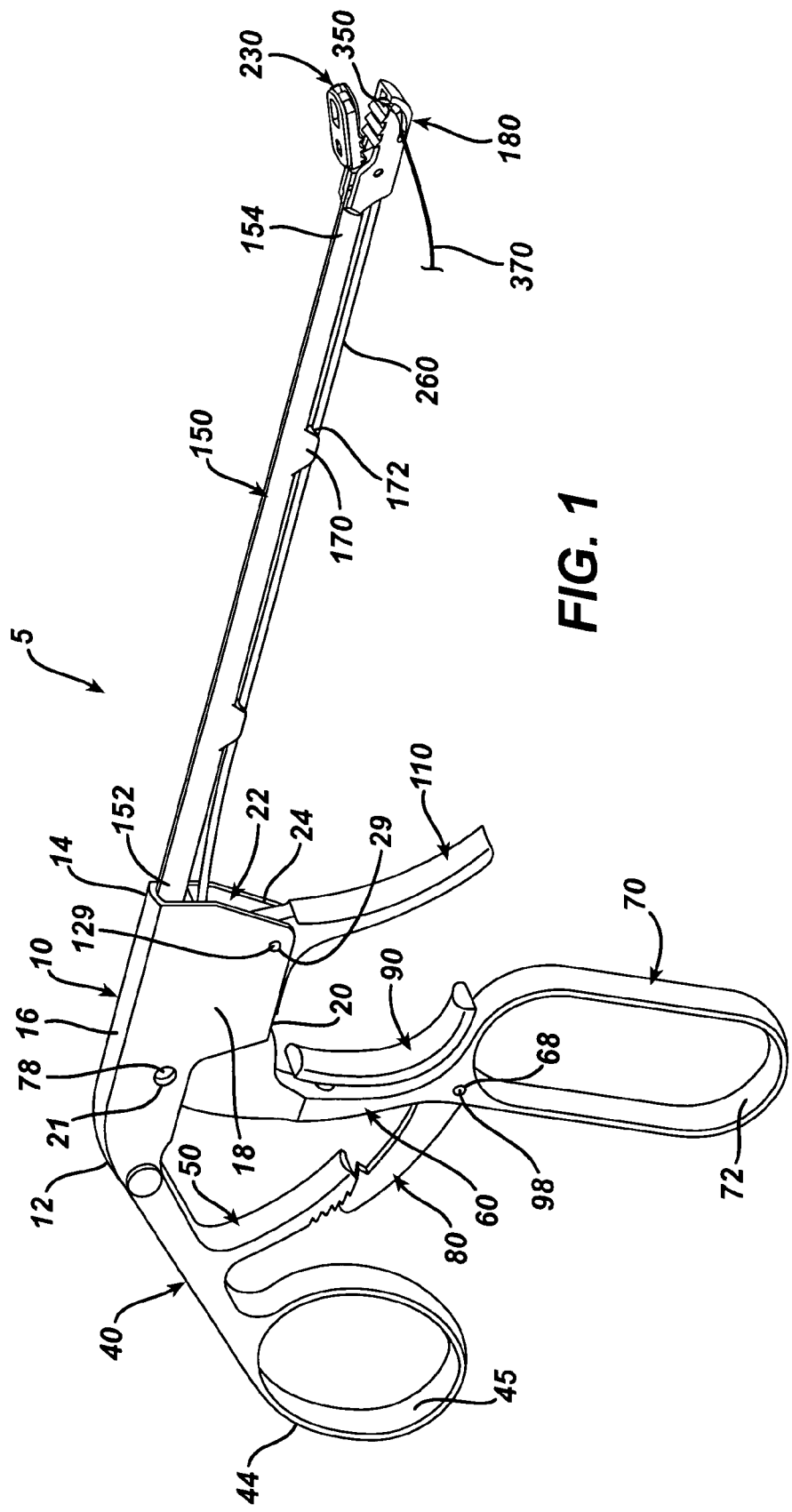
FIG. 1 is a perspective view of a grasper and needle passer instrument of the present invention.
Figure 2:
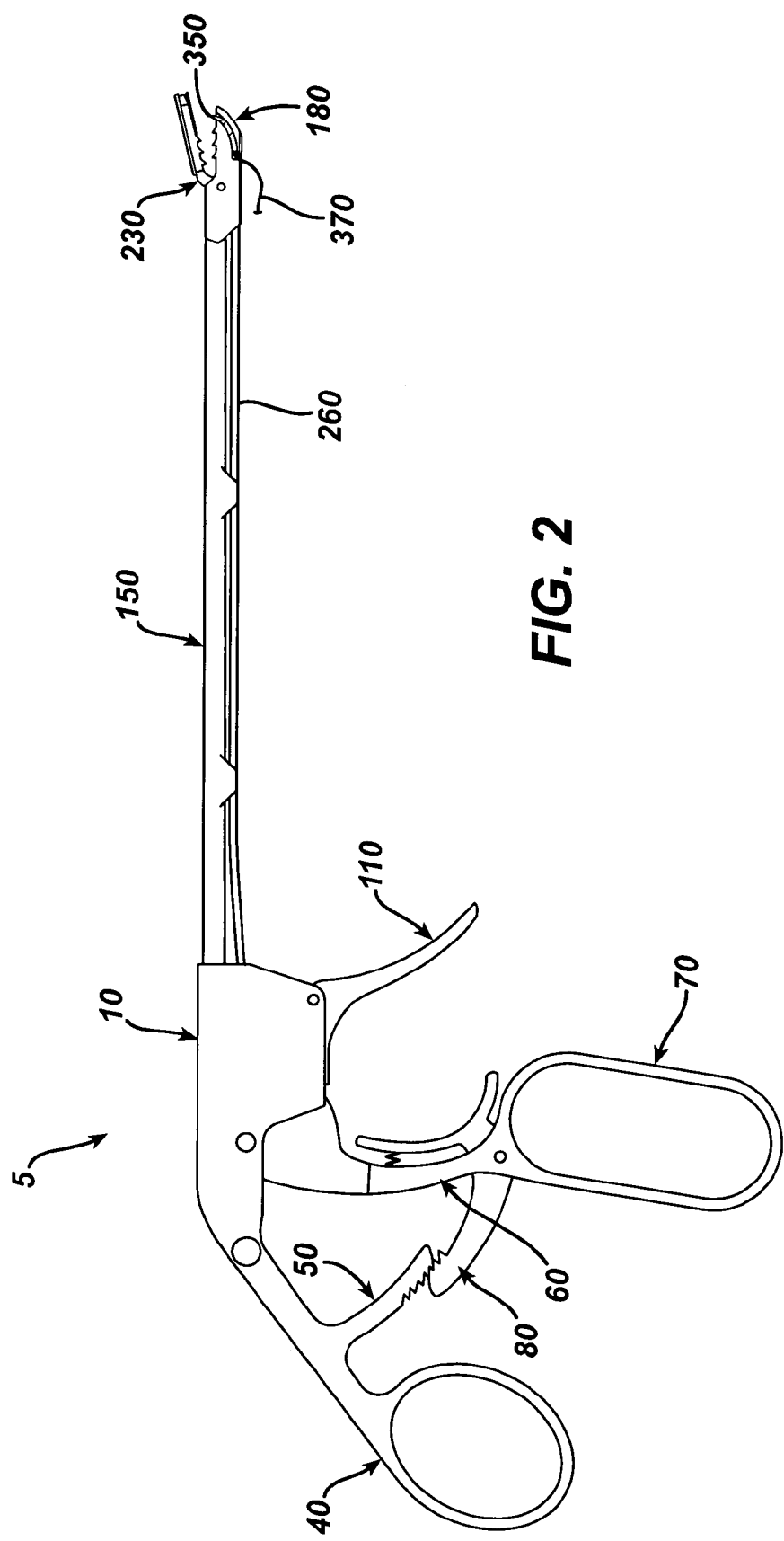
FIG. 2 is a side view of the tissue grasper and suture passer instrument of FIG. 1.
Figure 3A:
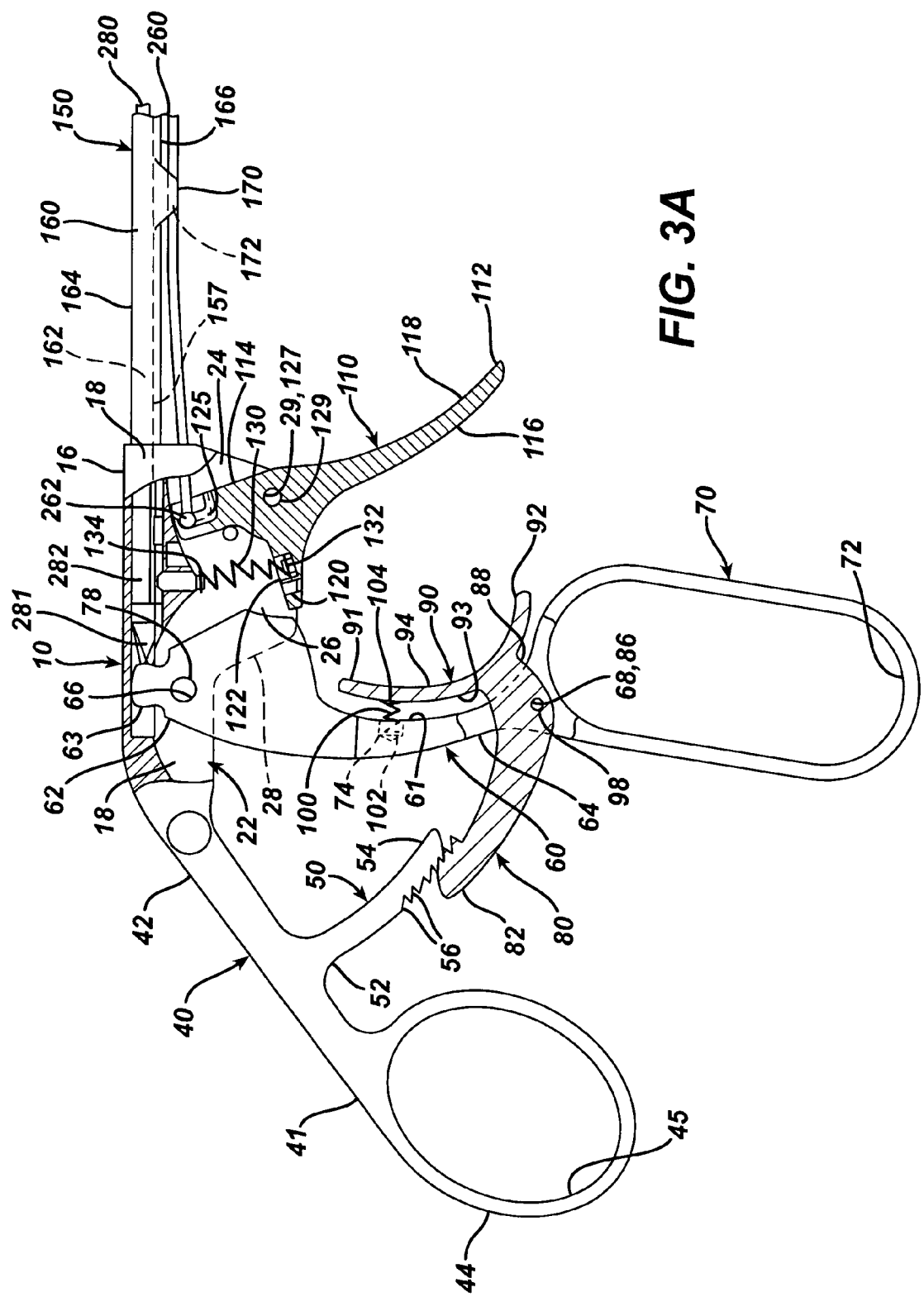
FIG. 3A is a partial cross-sectional view of the proximal end of the instrument of FIG. 2.
Figure 3B:
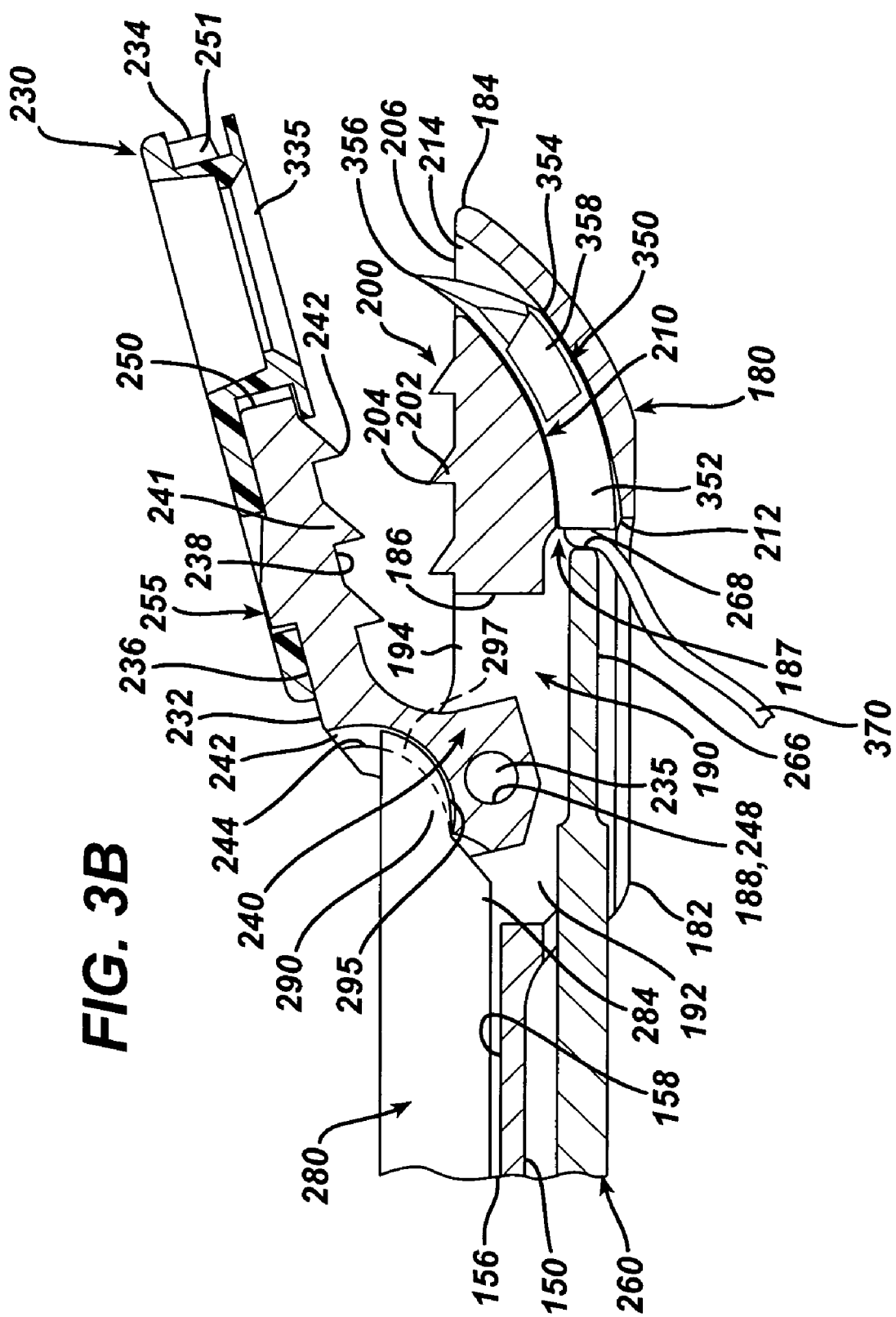
FIG. 3B is a partial cross-sectional view of the distal end of the instrument of FIG. 2.

The tissue grasper and suture passer instrument 5 of the present invention is illustrated in FIGS. 1–3. The instrument 5 is seen to have a frame member 10 having a proximal end 12, a distal end 14, a top 16, opposed lateral sides 18 and a bottom 20. Cavity 22 is contained within frame member 10. Cavity 22 is seen to have distal opening 24, bottom opening 26 and proximal opening 28. Openings 24, 26 and 28 are seen to be in communication with cavity 22. A pair of opposed trigger pivot pin openings 21 extend though the top of frame 10 and are in communication with cavity 20. In addition, a pair of opposed pivot pin openings 29 extend through the bottom of frame 10 and are in communication with cavity 22. Frame member 10 is also seen to have mounting cavity 30. Extending back and angulated down from the proximal end 12 of frame member 10 is the handle member 40. Handle member 40 is seen to have proximal end 41 and distal end 42. Extending from proximal end 41 is the optional finger ring 44 having opening 45. Also extending from the handle member 40 is the locking member engagement post 50. Engagement post 50 is seen to be preferably curved, having a proximal end 52, a distal rounded free end 54 and a plurality of teeth 56. The jaw actuation member 60 is seen to have upper end 62 and lower end 64. Upper end 62 has pivot pin hole 66 extending therethrough. Lower end 64 is seen to have pivot hole 68 extending therethrough. Extending from the lower end 64 of jaw actuation member 60 is the optional finger ring member 70 having opening 72. Spring retainer cavity 74 is seen to extend into member 60 through the distal side 61. The jaw actuation member 60 is seen to be pivotally mounted to frame member 10. More specifically, upper end 62 is seen to be mounted in cavity 22 by pivot pin 78 that extends through openings 21 in frame 10 and opening 68 in jaw actuation member 60.

The locking member 80 is seen to be pivotally mounted to actuation member 60. The locking member 80 is seen to be an "L" shaped member having a proximal end 82 and a distal end 88, however the member 80 may have other shapes if desired. Extending from the top surface of the proximal end of member 80 are the teeth 84. Teeth 84 are engageable with teeth 56 of locking member 50. Pivot pin mounting hole 86 is seen to extend transversely through member 80. Mounted to the proximal end 88 of locking member 80 is the disengagement member 90. Disengagement member 90 is seen to have a generally curved shape with top end 91. bottom end 92, proximal surface 93 and distal surface 94. Disengagement member 90 is mounted to actuation member 60 by pivot mounting pin 98 that is inserted through pivot pin mounting hole 86 and pivot pin hole 64. Helical spring 100 is seen to be mounted in cavity 74 such that the bottom 102 of spring member 100 is in contact with the bottom of cavity 74, and the top 104 of spring member 100 is in contact with the proximal surface 93 of member 90, thus exerting a biasing force against member 90. Also pivotally mounted in cavity 22 of frame 10 is the trigger member 110. The trigger member 110 is seen to have a bottom end 112, a top end 114, a proximal surface 116 and a distal surface 118. Extending proximally from the top end 114 is the lever member 120. Lever member 120 is seen to have second spring retention cavity 122. Extending through the upper end 114 of trigger member 110 are the slotted opening 125 and the pivot pin opening 127. The trigger member 110 is seen to be pivotally mounted in cavity 22 of frame 10 by the pivot pin 129 that extends through pivot pin mounting opening openings 29 in frame 10 and pivot pin opening 127 in trigger member 110. Spring member 130 is seen to have bottom 132 and top 134. The spring member 130 is mounted in spring retention cavity 122, and the bottom 132 exerts a biasing force against lever member 110 through lever member 120.

Extending from the distal end 14 of frame 10 is the elongated member 150. Elongated member 150 is seen to have a proximal end 152, a distal end 154 and a longitudinal slot 156 therein extending along the length of member 150 and having proximal opening 157 and distal opening 158. The elongated member 150 is seen to have outer surface 160 and inner surface 162, as well as top 164 and bottom 166. The proximal end 152 of elongated member 150 is seen to be mounted in frame 10 in cavity 30. Although it is preferred that proximal end 152 be fixedly mounted, alternatively, the end 152 may be mounted to provide for rotational movement or longitudinal movement of tubular member 150. Extending downward from the outer bottom 166 of elongated member 150 are the grommet members 170 having longitudinal passages 172.

Referring also now to FIGS. 3B and 4–15, seen to be extending from the distal end 154 of elongated member 150 is the lower jaw member 180. The lower jaw member 180 is seen to have proximal end 182 and distal end 184, and a pair of opposed sides 188 and 189, top 186 and bottom 185. Lower jaw member 180 is seen to have cavity 190 having proximal opening 192 and top opening 194, both of which are in communication with cavity 190. Cavity 190 is seen to have distal end 196 adjacent to inner wall 186. The needle passage opening 187 is contained in wall 186. Extending transversely through jaw member 180, and in communication with cavity 190, are the pivot pin mounting holes 188. The jaw member 180 is seen to have top grasping surface 200. Extending up from the surface 200 are the tissue engagement teeth 202 having tips 204. Surface 200 is seen to have needle opening 206. Also contained in the lower jaw member 180 is the needle passageway 210 having proximal and distal ends 212 and 214, respectively. The proximal end 212 of passageway 210 is in communication with opening 187 and the distal end 214 is in communication with opening 206. Preferably, the passage has an opening 218 extending out through the side 188 of jaw member 180 to facilitate the loading and passage of a needle and suture. The opening 218, although not preferred, may be located on the bottom 185 of jaw member 180. Optionally, there are multiple openings 218. The upper jaw member 230 is seen to be pivotally mounted to lower jaw member 180. The upper jaw member 230 is seen to have proximal end 232, distal end 234, upper surface 236 and bottom surface 238. Extending down from the bottom surface 238 are the tissue engagement teeth 241 having tips 242. Extending down and proximally from distal end 232 of the upper jaw member 230 is the camming member 240. The camming member 240 is seen to have concave curved top camming surface 249. Contained in surface 249 is the longitudinal retention groove 244. The pivot hole passage 248 is seen to be contained in the bottom of the camming member 240. The upper jaw member 230 is mounted in cavity 190 by inserting pivot pin 235 though pivot pin openings 188 and pivot hole passage 248. The upper jaw 230 is seen to have U-shaped slot 250 having opening 251. Extending up from the upper surface 236 of jaw member 230 is the cartridge retainer member 255. Retainer member 255 is seen to have top 256 and distal ramped surface 257. The member 255 has opposed sides 258 connected by curved ends 259.

Slidably mounted in the passages 172 of grommet member 170 is the needle actuator rod 260. Rod 260 is seen to be an elongated rod-like member having a proximal end 262 and a distal end 266 having a distal needle engagement nose 268. Distal end 266 is seen to be optionally necked down and has a smaller diameter than that of rod 260. The proximal end 262 of rod 260 is seen to pivotally mounted in cavity 22 of frame 10 in slotted opening 125 in trigger member 110.

The jaw actuation rod 280 is seen to have distal end 284 and proximal end 282. The jaw actuation rod 280 is a rod-like member that is slidably mounted in longitudinal slot 156 of elongated member 150. The proximal end 282 of actuation rod 282 is pivotally mounted to the top section 62 of jaw actuation member 60 by pin member 281 extending proximally from proximal end 282 and engaged by nub 63 extending up from the top 62 of jaw actuation member 60. Extending distally from the distal end 284 of actuation rod 280 is the cam member 290 having camming surface 295. The tongue member 297 is seen to extend out from surface 295, and to be engaged in retention groove 244 of camming member 240.

Figure 4:
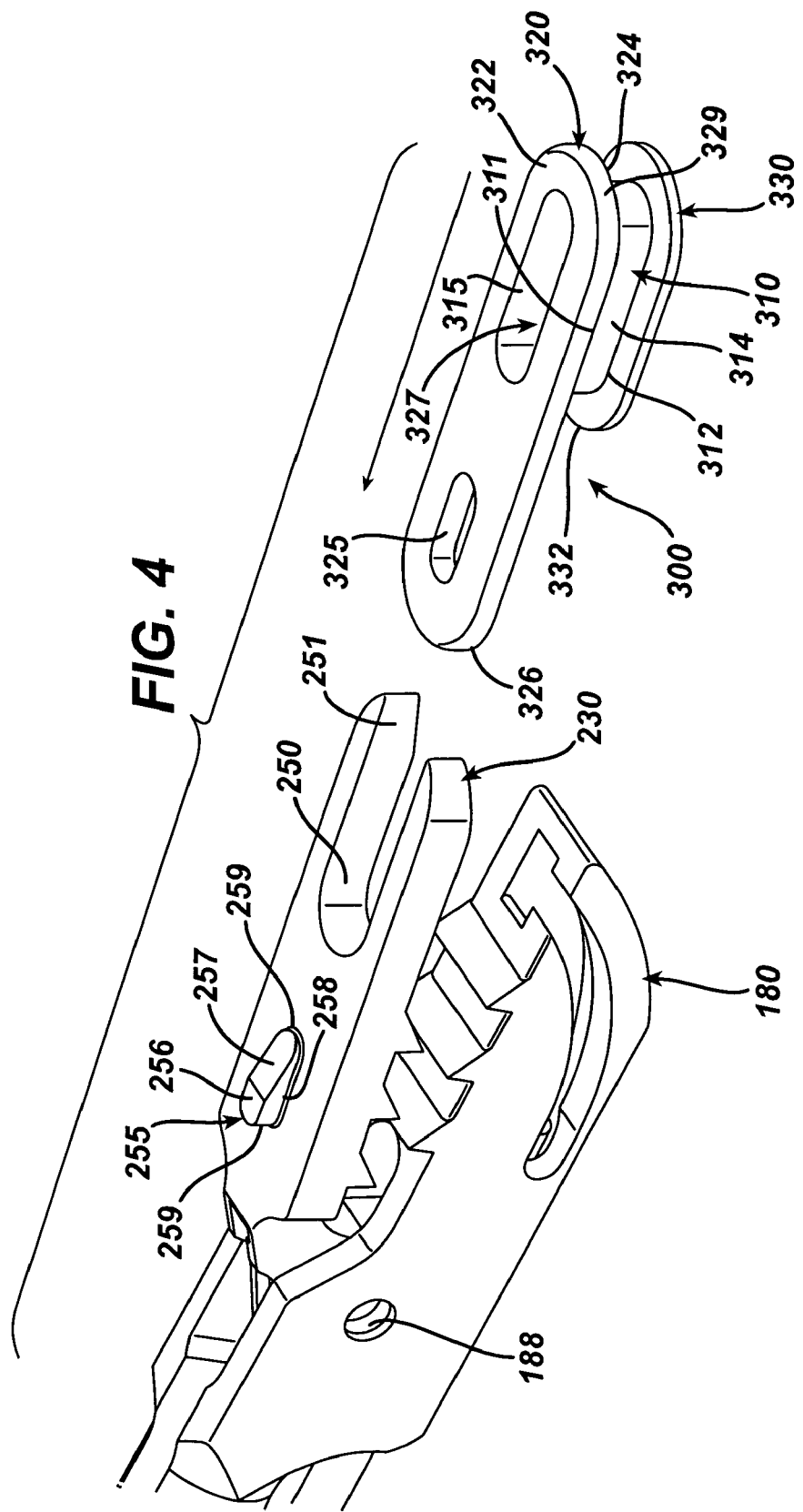
FIG. 4 is a magnified exploded perspective view of the distal end of the tissue and suture passer instrument of the present invention illustrating the upper and lower jaws of the instrument and a needle clip cartridge that is mounted to the upper jaw.
Figure 5:
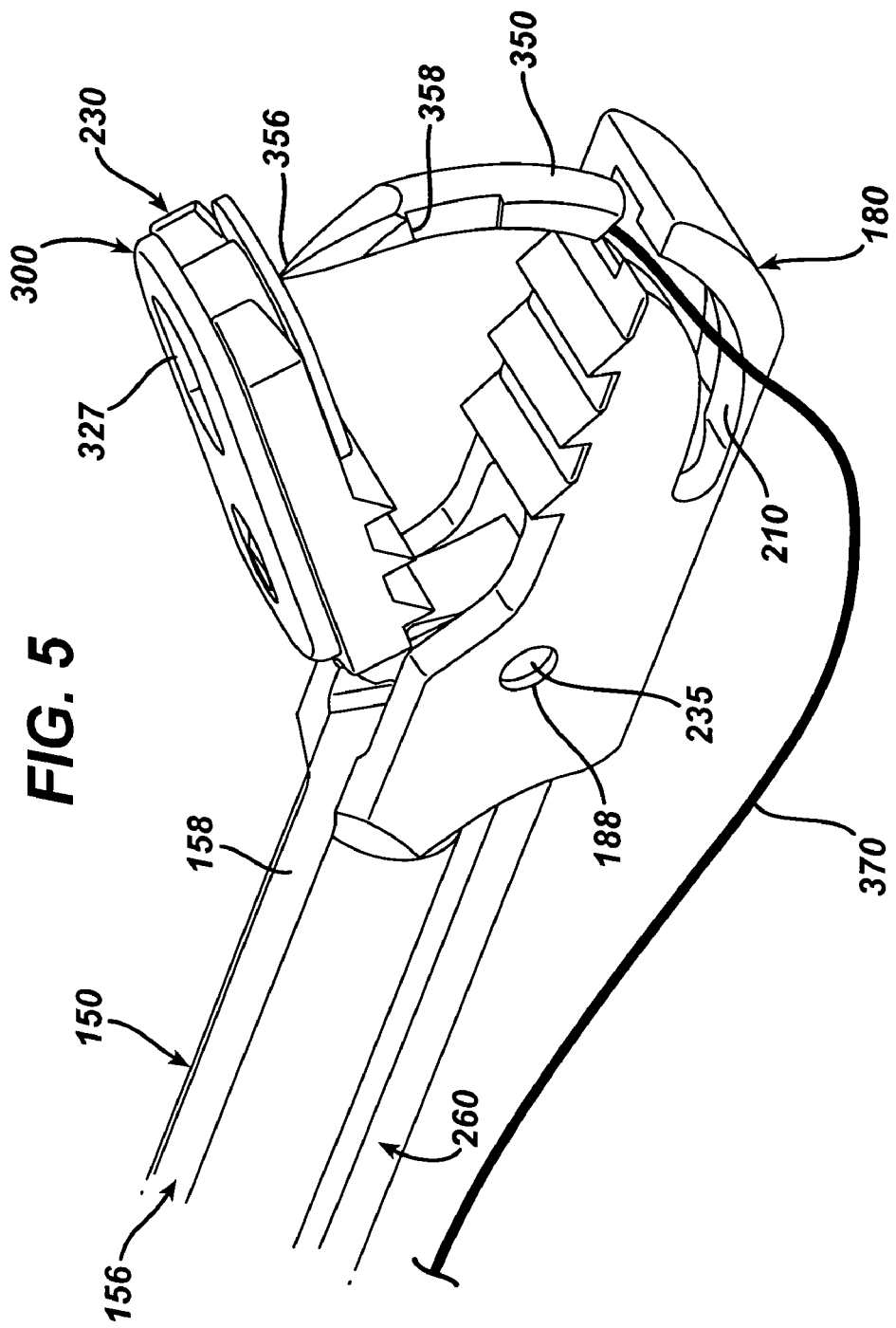
FIG. 5 illustrates a surgical needle and suture prior to mounting in the lower jaw of the instrument.
Figure 6:
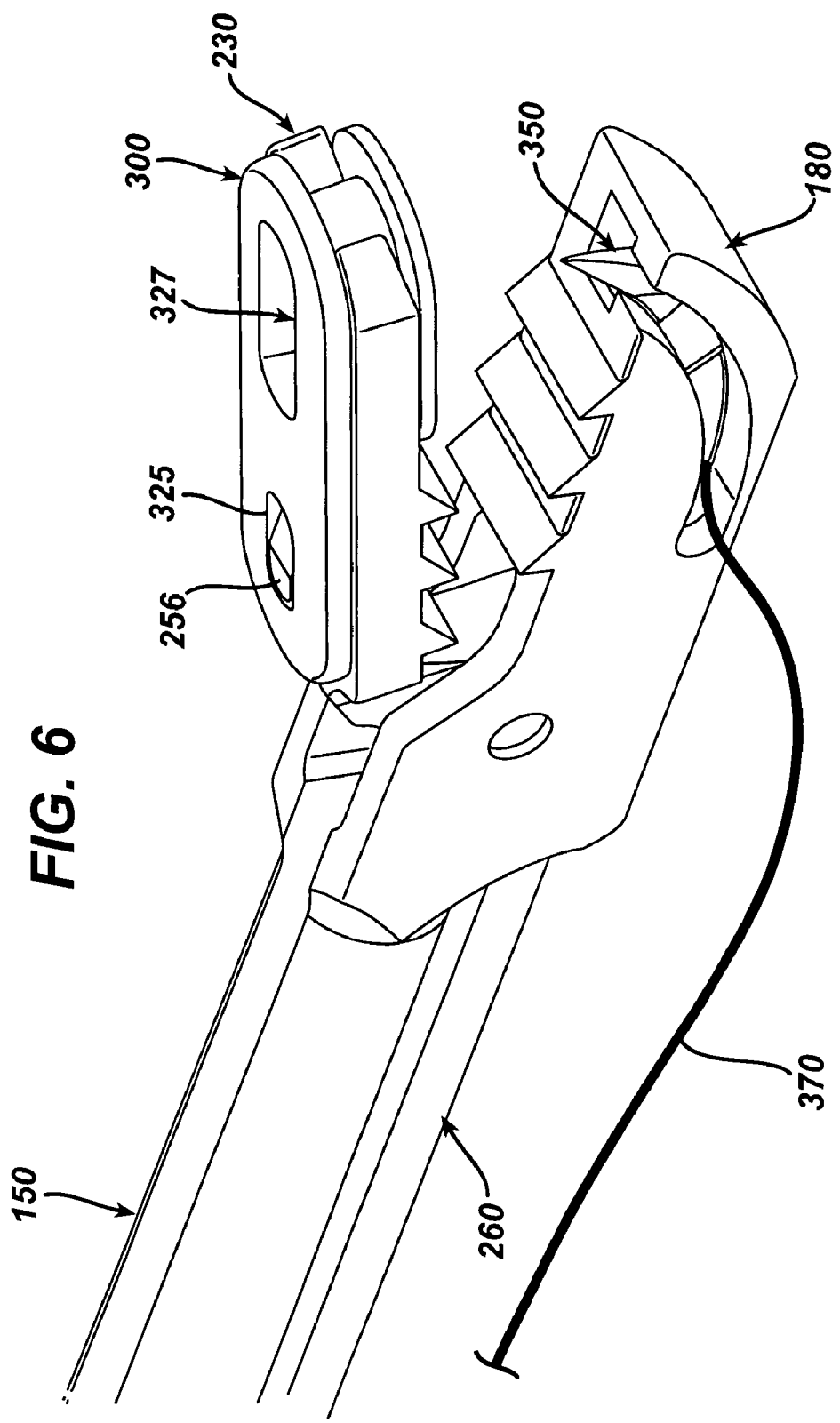
FIG. 6 illustrates the distal end of the instrument in an armed configuration with the needle cartridge mounted in the upper jaw and the surgical needle mounted in the lower jaw with the upper jaw open and ready to receive tissue.
Figure 7:
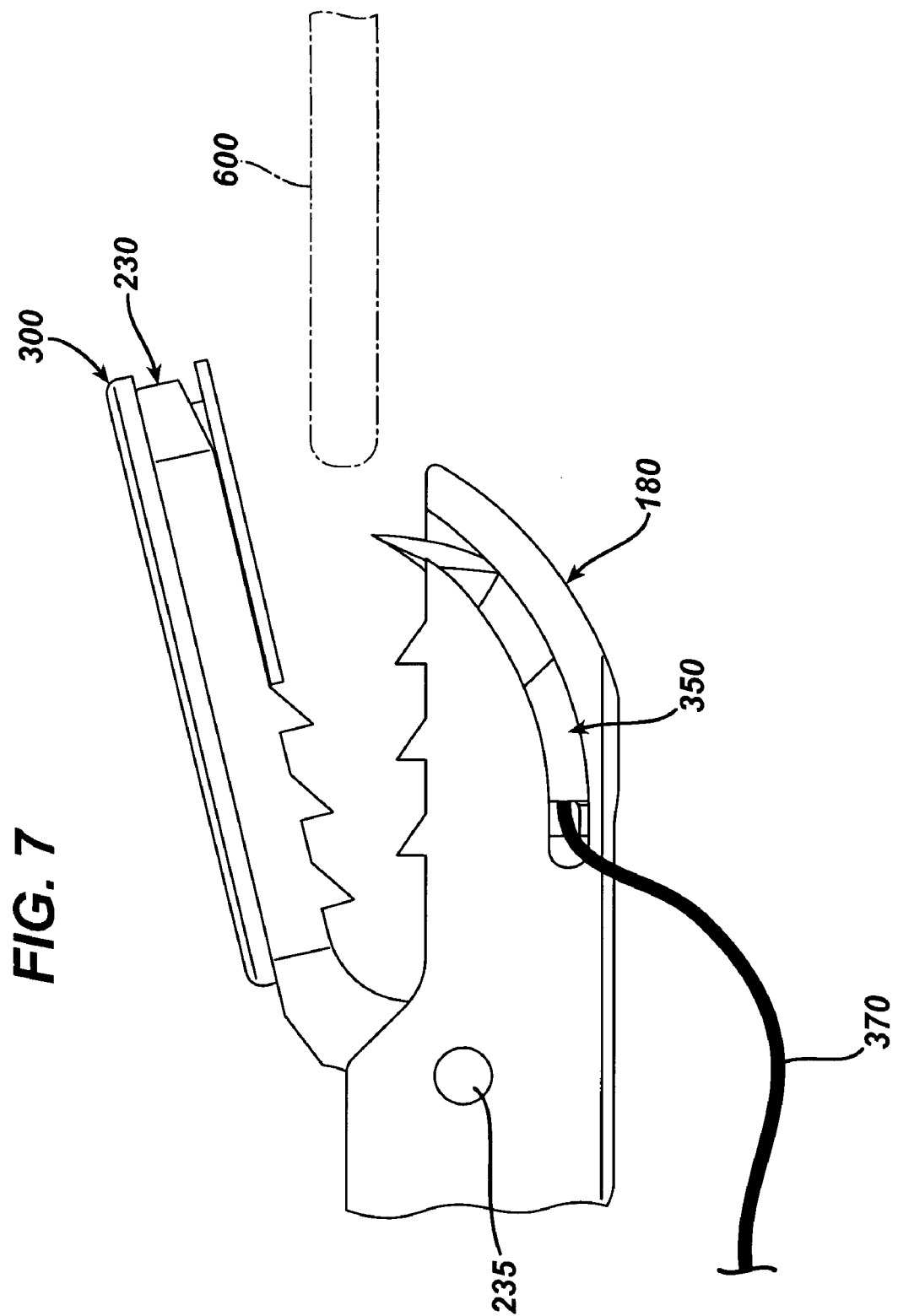
FIG. 7 illustrates the distal end of the armed instrument in proximity to tissue that will be grasped and sutured.
Figure 8:
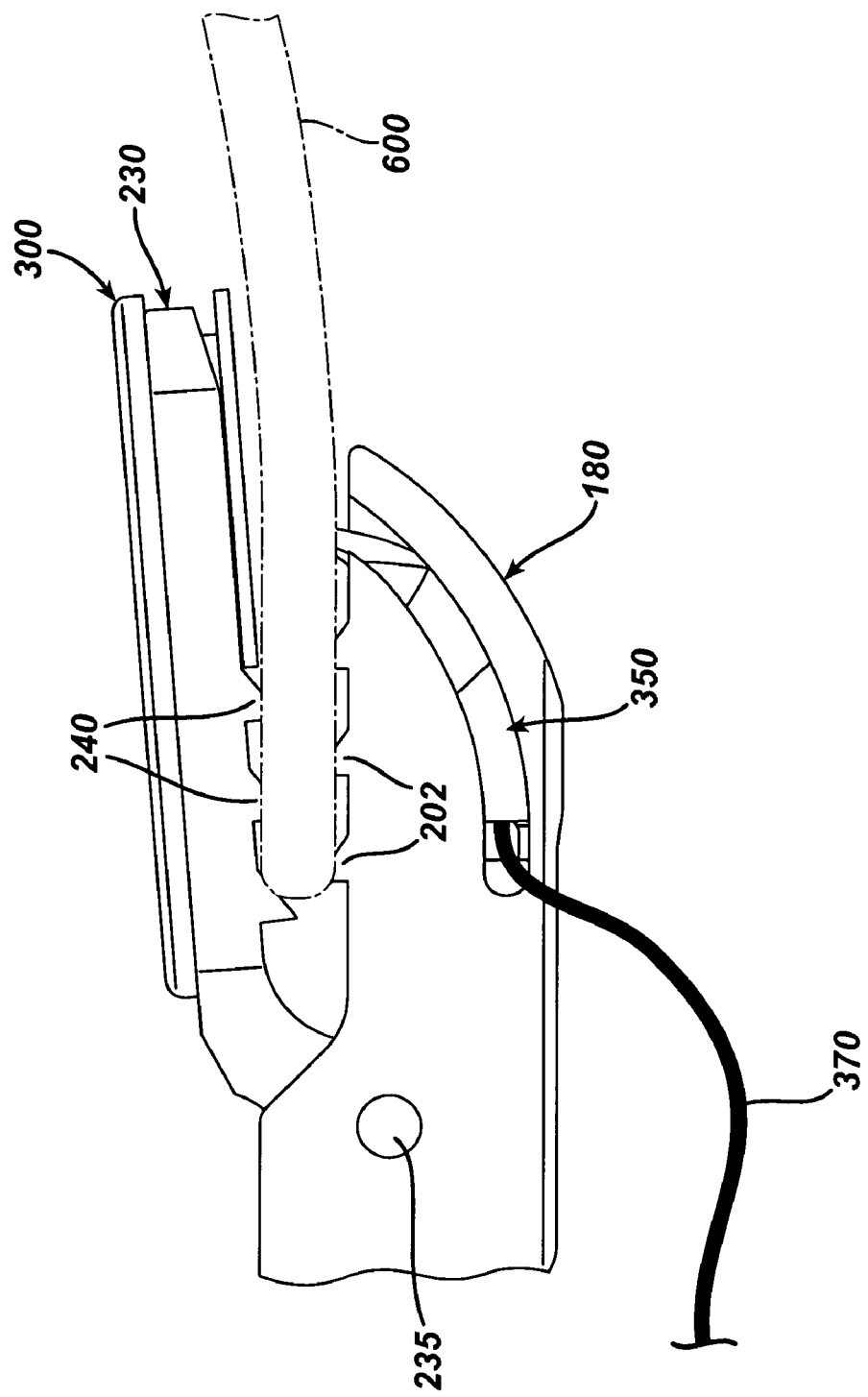
FIG. 8 is a partial side view illustrating the instrument grasping the soft tissue between the jaws, prior to engaging the needle.
Figure 9:
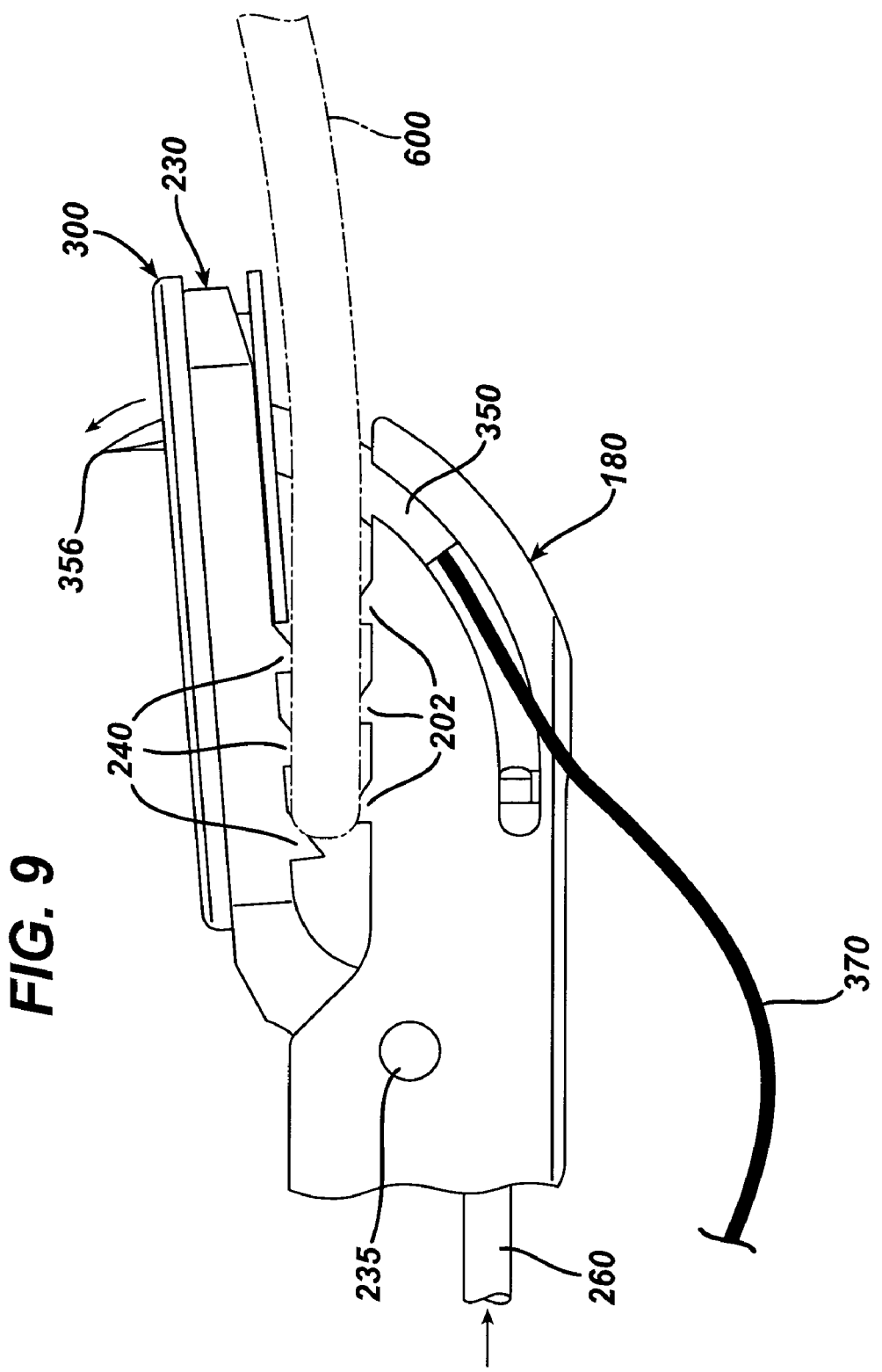
FIG. 9 is a side view of the instrument illustrating the needle deployed through the tissue, with the distal end of the needle engaged and locked by the cartridge in the top jaw.
Figure 10:
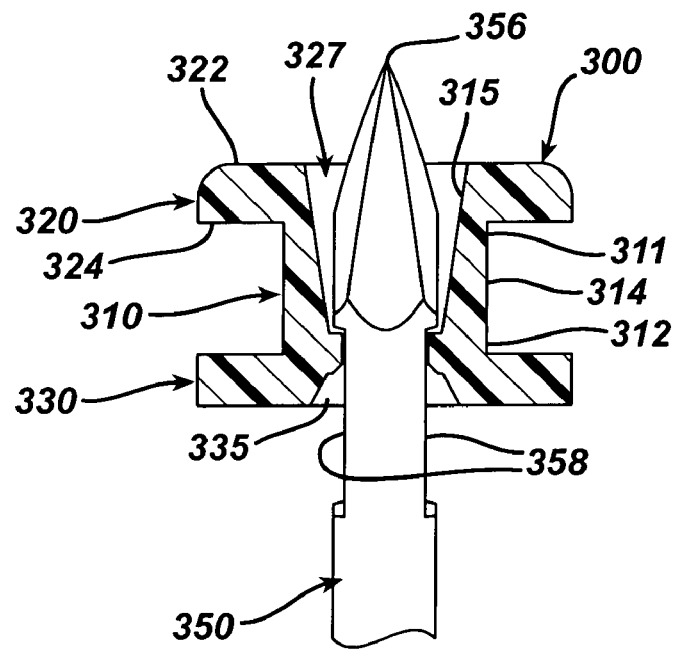
FIG. 10 is a partial transverse cross-sectional view of the instrument of FIG. 9, illustrating the needle engaged in the cartridge.
Figure 11:
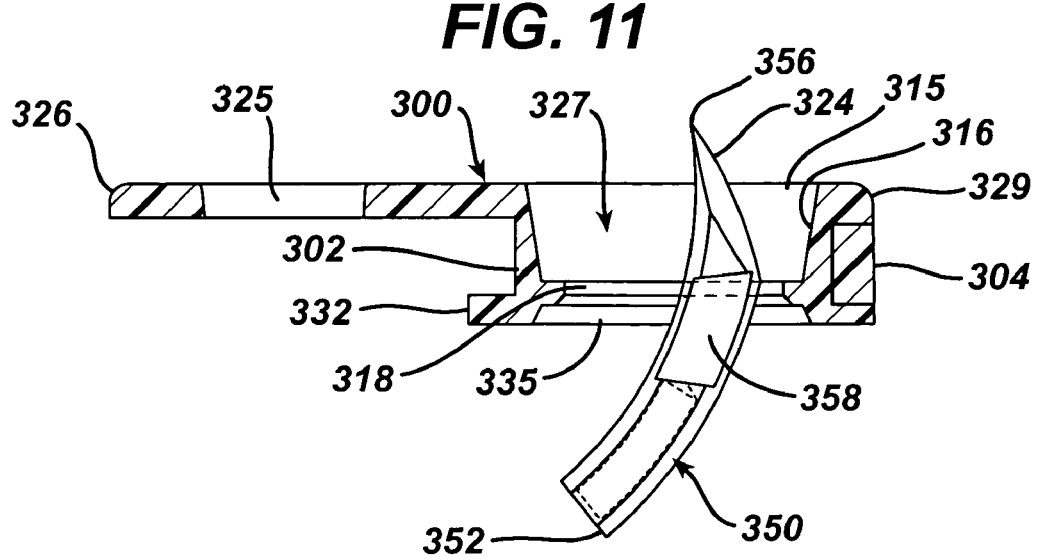
FIG. 11 is a partial longitudinal cross-sectional view of the cartridge of FIG. 10, illustrating the needle engaged by the cartridge.
Figure 12:
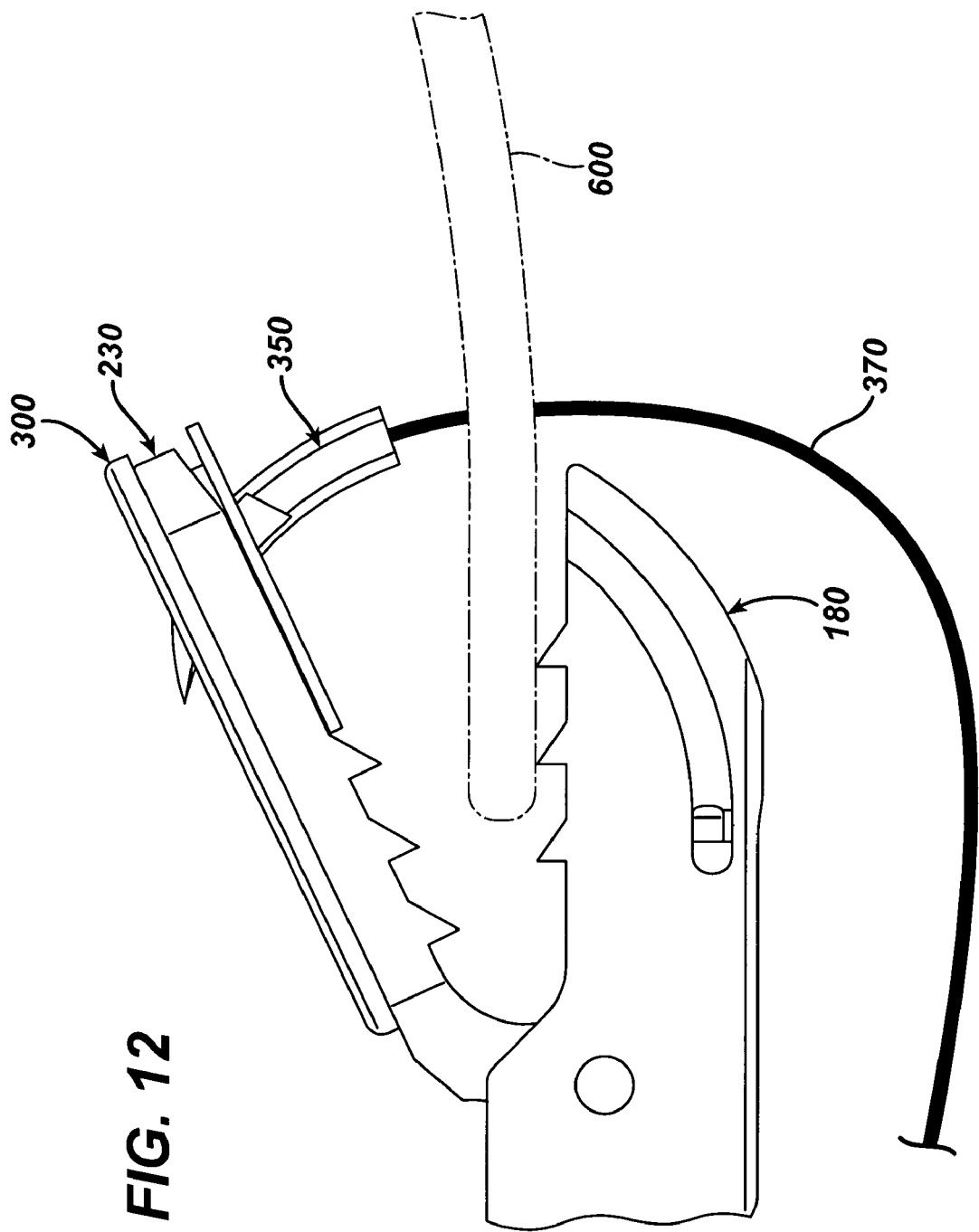
FIG. 12 illustrates the upper jaw of the instrument rotated to the raised position with the needle exited from the tissue and the suture passing through the tissue.
Figure 13:
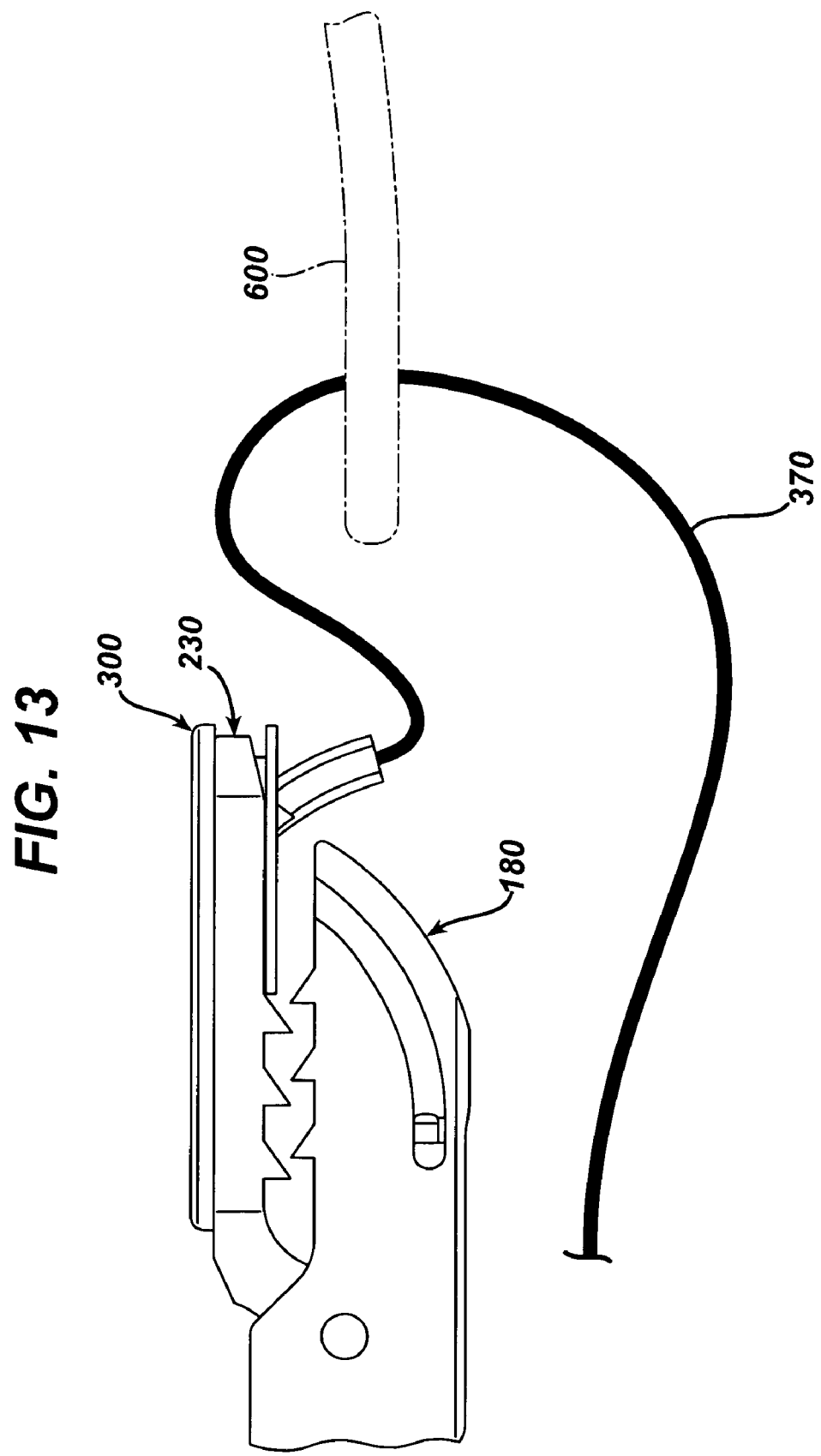
FIG. 13 illustrates the instrument of FIG. 12, wherein the instrument has been pulled back away from the tissue, causing an additional length of the suture to be pulled or passed through the tissue.
Figure 14:
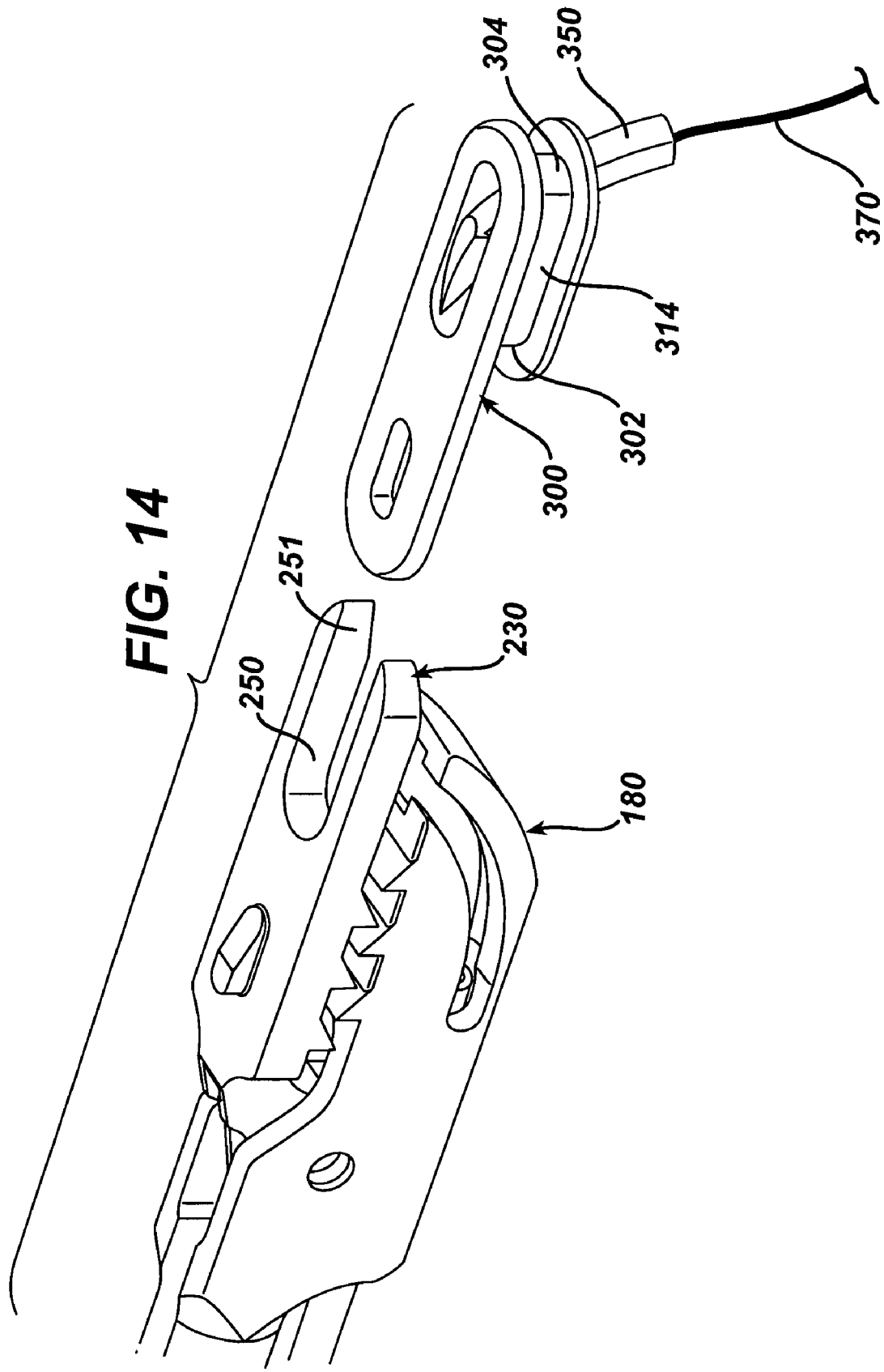
FIG. 14, is a perspective view of the distal end of the instrument of the present invention after the cartridge has been removed from the upper jaw and the needle has been cut away from the suture.

The needle cartridge 300 is seen in FIG. 4. The cartridge 300 is seen to have member 310 having cavity 315. Although cavity 315 preferably has a circular cross-section as shown, the cavity 315 my have other geometric cross-sections including but not limited to square, polygonal, rectangular, triangular, oval and the like and combinations thereof. Cartridge 300 is seen to have proximal end 302 and distal end 304. Member 310 is seen to have top 311, bottom 312, and exterior surface 314 and interior surface 316. Extending into the cavity 315 is the annular engagement tab ring member 318. Although it is preferred that the tab ring member 318 have an annular configuration, other configurations may be used including tab segments, or other geometric configurations depending on the configuration of the cavity 315. Mounted to the top 311 of cartridge 300 is the upper flange 320 having top surface 322, bottom surface 324, proximal end 326 and distal end 329. Extending through flange 320 is the needle opening 327 in communication with cavity 315. Seen to extend through the proximal end 326 of flange 320 is the retainer opening 325. Bottom flange 330 is seen to be mounted to the bottom 312 of member 310, and has opening 335 in communication with cavity 315, as well as proximal end 332 and distal end 334. The cartridge 300 is mounted to jaw member 230 by sliding the proximal end 326 of flange 320 over the top surface 236 of jaw member 230 such that the member 310 slides into slot 250, and opening 325 is engaged by retention member 255, such that the top flange 320 is partially on top of and bottom flange 330 is partially below upper jaw member 230.

The instrument 5 is armed for passing a needle 350 and attached suture 370 through tissue by inserting a needle 350 in needle passageway 210 of jaw member 180. The needle 350 is seen to have distal end 354 and proximal end 352 extending from the proximal end 352 of needle 350 is the suture 370. Extending distally from the distal end 354 of needle 350 is the pointed piercing end 356. Needle 356 is seen to have opposed undercuts 358 to facilitate locking in cavity 315 of cartridge 300. The needle 350 is mounted in jaw member 180 such that the distal piercing end 354 extends at least partially out of passage 210 and through opening 206 and above grasping surface 200. The needle 350 is seen to preferably have a curved configuration to conform to the needle passageway 210, but may also be made of a resilient material such as spring stainless steel or a superelastic shape memory material such as Nitinol, and may have a substantially straight configuration. The cartridge 300 is then mounted to upper jaw 230 by sliding member 310 into slot 250 such that the flanges 320 and 330 are above and below the top and bottom surfaces of jaw member 230, and such that retainer opening 325 is engaged by retention member 255, and thereby substantially fixed in place with respect to jaw member 230.

The suture 370 may be mounted to needle 350 in a conventional manner, including swaging the distal end 374 of suture in a drilled hole or channel in the proximal end 352 of needle 350, threading the suture 370 through an eyelet, etc. Any conventional sutures may be used including non-absorbable sutures made from conventional biocompatible polymers and bio-absorbable sutures made from conventional bio-absorbable and resorbable polymers.

When armed, the instrument 5 operates in the following manner. The surgeon grasps the instrument 5 by the handle member 40 and places a thumb within opening of thumb ring 44. One or more of the other fingers of the hand are placed through opening 72 of finger loop 70. Tissue 500 is grasped between the upper jaw member 230 and the lower jaw member 180 by pulling back on the actuation member 60 causing the actuation member 60 to pivot about pivot pin 78 causing jaw actuation rod 280 to be displaced distally in the slot 157 of elongated member 150. This causes the camming member 290 of actuation rod 280 to engage the camming surface 242 of camming member 240, thereby causing the jaw member 230 to rotate about pivot pin 235 toward lower jaw member 180. The opposite rotation of the jaw actuation member 60 causes the actuation rod 280 to slide and move proximally causing the top jaw to rotate open. The tissue 600 is engaged by teeth 202 extending from the upper surface 200 of jaw member 180 and the teeth 241 extending downward from the bottom surface 238 of jaw member 230. The tissue 500 is also partially pierced by the piercing point 356 of needle 350. The spatial position of jaw 180 relative to jaw 230 is maintained by the locking member 80 and the engagement post 50 which are engaged by the teeth 56 and 84 in a ratcheting manner. The needle 350 and suture 370 are passed through tissue 600 by the surgeon engaging or pulling back on trigger member 110 thereby rotating the trigger member 110 about pivot pin 129. This is seen to cause the actuation rod 260 to move distally through the passages 172 of grommet members 170. The needle engagement nose 268 of distal end 266 then engages the distal end 352 of needle 350 pushing it through 210, and out through opening 206, through tissue 500 and into passage 315 of member 310 of cartridge 300 and partially out through opening 327 such that the undercuts 358 are engaged by the ring tab member 318. Next the surgeon opens jaw 230 by first unlocking the jaw 230 by pulling back on disengagement member 90 causing locking member 80 to disengage from engagement post 50, and then moving finger loop 70 distally to rotate the jaw 230 open. This causes the needle 350 to move completely through tissue 600 and move the suture 370 through tissue 500. The surgeon then cuts the suture 370 away from needle 350 and cartridge 300, completing the passage of the suture 370 through the tissue 600. If desired, the instrument 5 can be re-armed with a new needle 350 and attached suture 370 along with a new cartridge 300 to provide for multiple suture passes.

In an alternate embodiment of the cartridge 300 of the present invention is seen in FIGS. 15–20. The cartridge 500 is seen to have a member 510 having a cavity 515. Cavity 515 has an elongated slot section 520 communicating with a proximal circular opening 522. Opening 522 may have other geometric configurations as well. Tab engagement members 530 are seen to extend into slot section 520 to engage a surgical needle. The tab engagement members 530 are not present in the opening 522. Cartridge 500 is seen to have proximal end 502 and distal end 504. Member 510 is seen to have top 511, bottom 512 and exterior surface 514 and interior surface 516. Mounted to the top 511 of cartridge 500 is the upper flange 540 having top surface 542, bottom surface 544, proximal end 546 and distal end 549. Extending through upper flange 540 is the needle opening 547 in communication with cavity 515. Seen to extend through the proximal end 546 of upper flange member 540 is the retainer opening 545. Bottom flange 550 is seen to be mounted to the bottom 512 of member 510, and has opening 555 in communication with cavity 515, as well as proximal end 562, and distal end 564. The cartridge 500 is mounted to upper jaw member 230 of instrument 5 by sliding the proximal end 546 of upper flange 540 over the top surface 236 of jaw member 230 such that the member 510 slides into slot 250, and retainer opening 545 is engaged by retention member 255, such that top flange 540 is substantially on top of bottom flange 550 is substantially below upper jaw member 230. In use with instrument 5 to pass a needle and suture through tissue, after surgical needle 350 is engaged in the elongated slot section 520, the distal end 354 of the needle having the undercuts 358 can be moved or slid in slot section 520 into opening 522 where the undercuts 358 of the needle 350 are disengaged from the engagement tab members 530. The needle 350 can then be removed from the cavity 522 (without cutting the attached suture) and reloaded into the needle receiving passage of the lower jaw, thereby re-arming the instrument 5 for additional or multiple suture passes using the same needle 350 and suture and cartridge. The cartridge member 500 may be removed from upper jaw 230 prior to removing the suture from cavity 522, and then remounted in slot 250 to rearm the instrument 5 for additional suture passes.

The suture passer instruments of the present invention can be used in a variety of minimally invasive procedures including arthroscopic, endoscopic, laparoscopic and the like. One common arthroscopic procedure that the suture passers of the present repair can be utilized is an arthroscopic Bankart repair. An arthroscopic surgical Bankart repair procedure is disclosed in the following journal article which is incorporated by reference: "Arthroscopic Bankart Repair Using Suture Anchors", Eugene M. Wolf, M.D., Richard M. Wilk, M.D. and John C. Richmond, M.D., *Operative Techniques in Orthopaedics*, Vol. 1, No. 2 (April), 1999:pp. 184–191.

The following example is illustrative of the principles and practice of the present invention, although not limited thereto.

EXAMPLE

Figure 15:
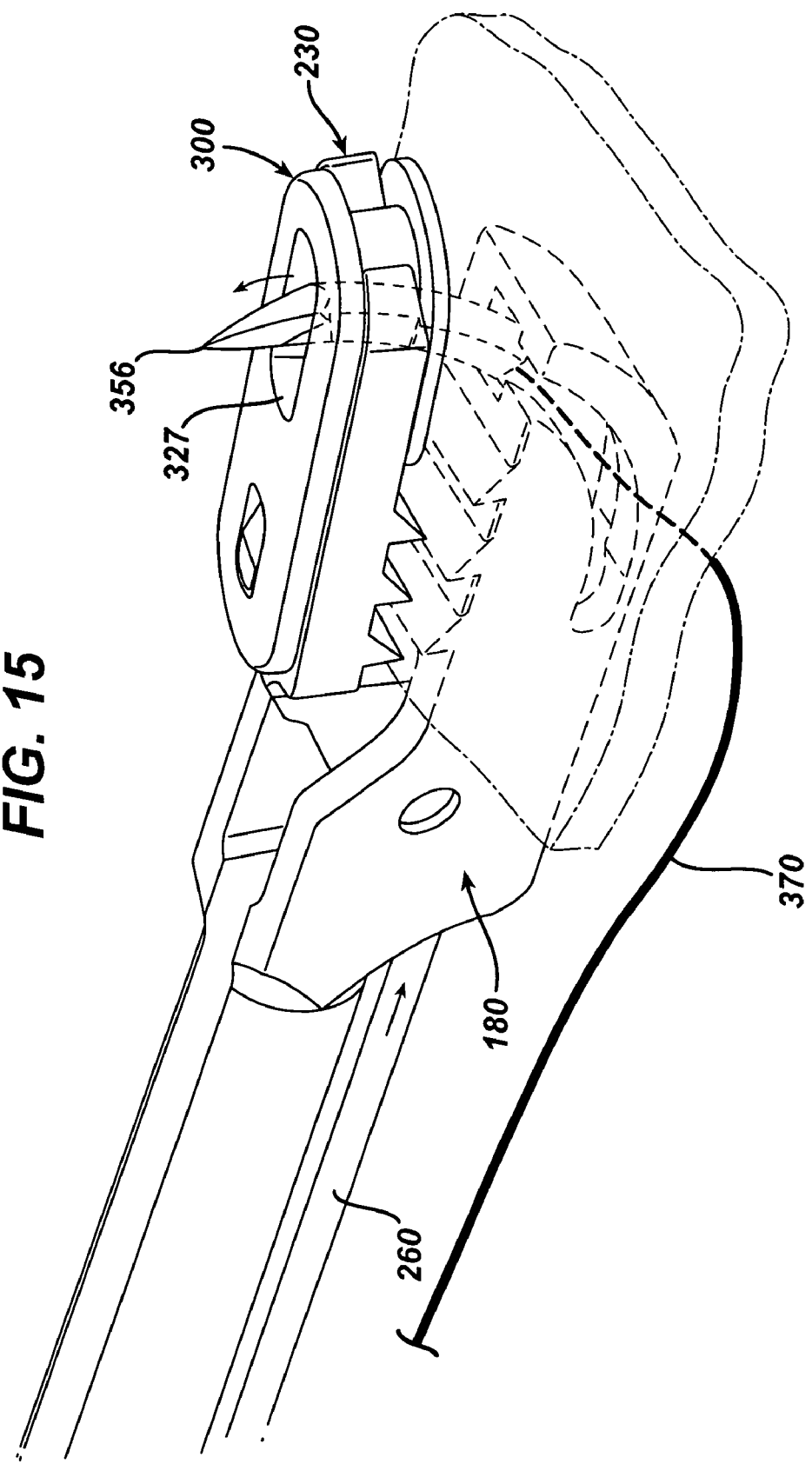
FIG. 15 illustrates the instrument of the present invention inserted into a patient's shoulder and passing a needle and suture through the patient's ligament labral complex to effect a Bankart repair procedure
Figure 16:
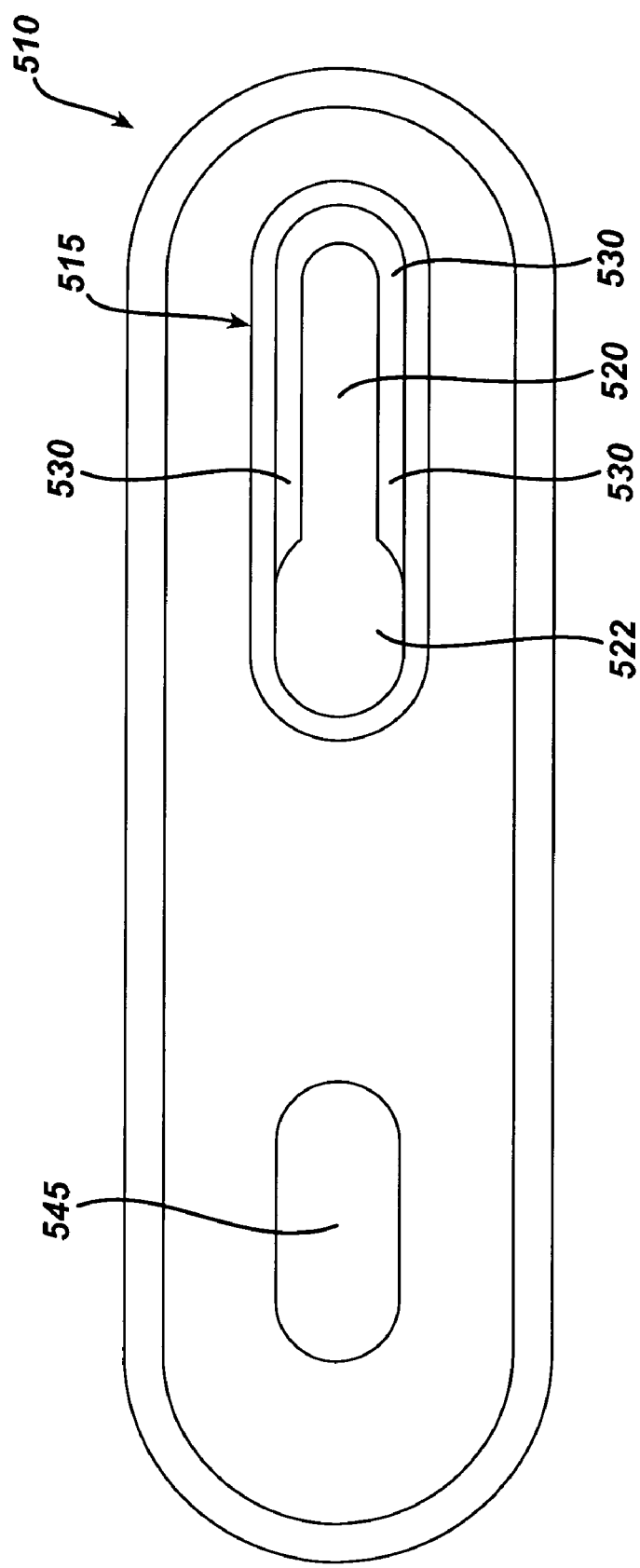
FIG. 16 is a top view of an alternate embodiment of a cartridge that can be used with the suture passer instruments of the present invention; the cartridge has an elongated slot for engaging a needle and a proximal opening such that the needle can be moved along the slot into the proximal opening and removed from the cartridge.
Figure 17:
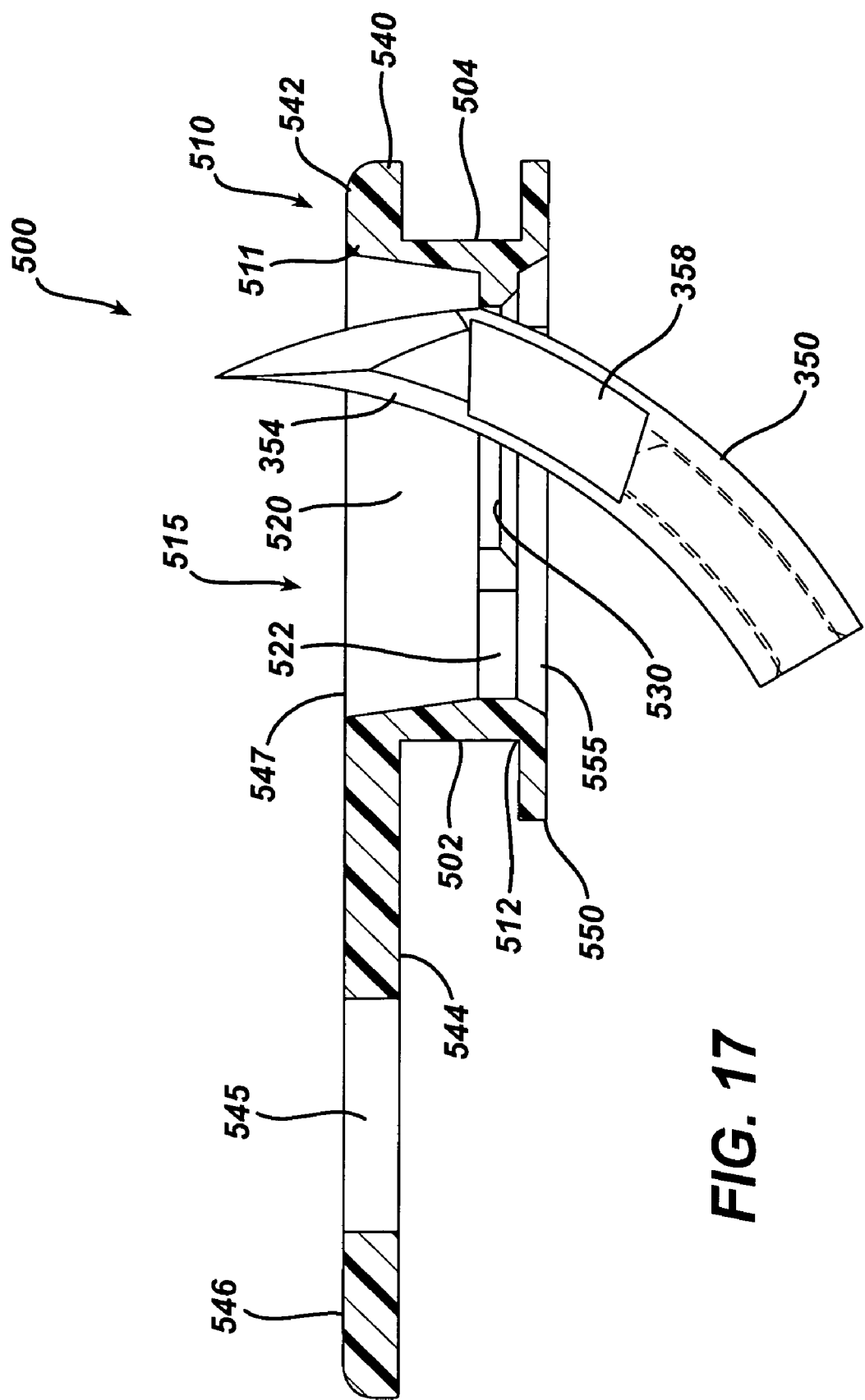
FIG. 17 is a partial, cross-sectional view of the cartridge of FIG. 16, illustrating a needle engaged in the slot.
Figure 18:
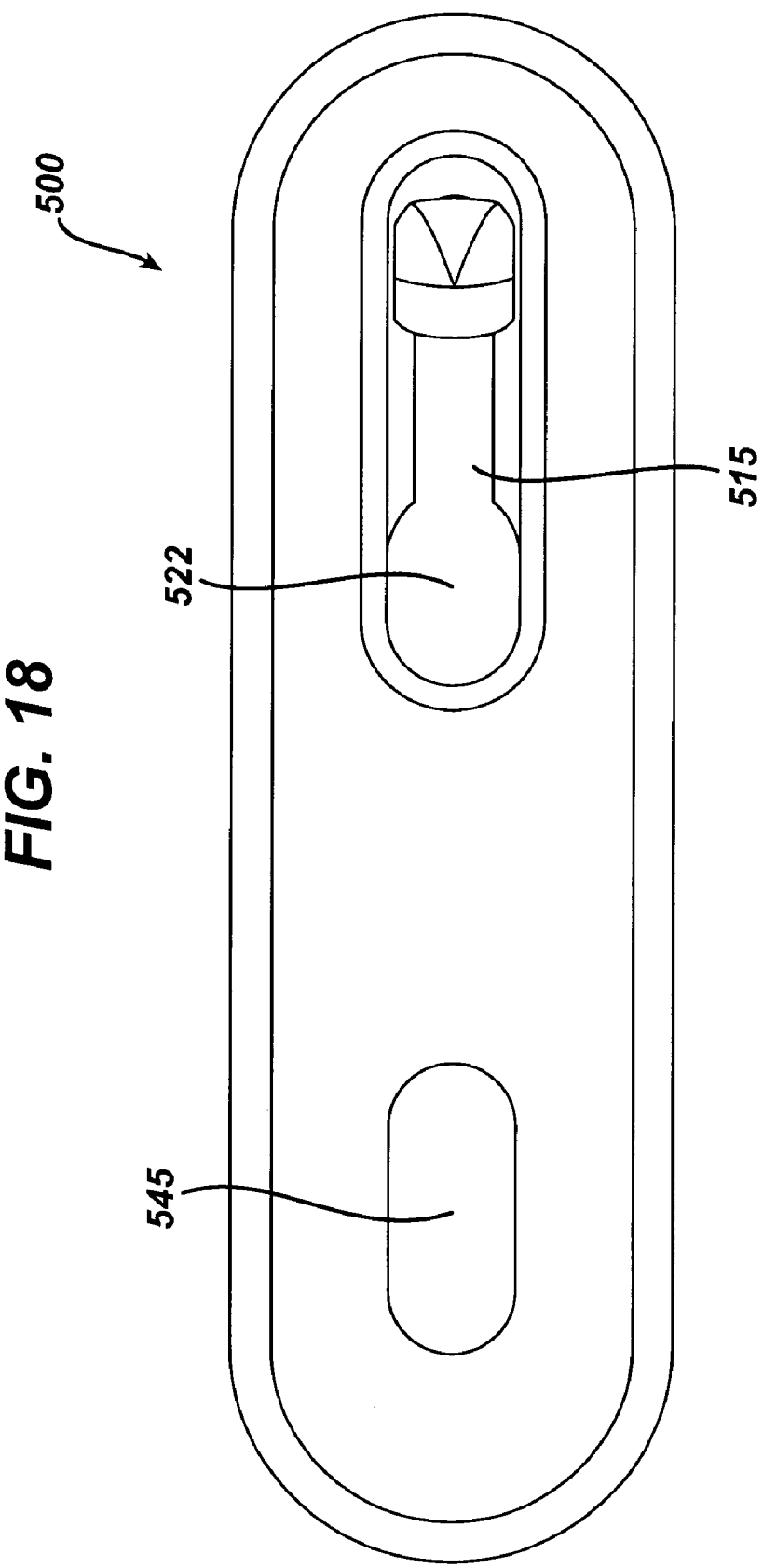
FIG. 18 is a top view of the cartridge of FIG. 16, illustrating the distal end of a needle engaged in the slot.
Figure 19:
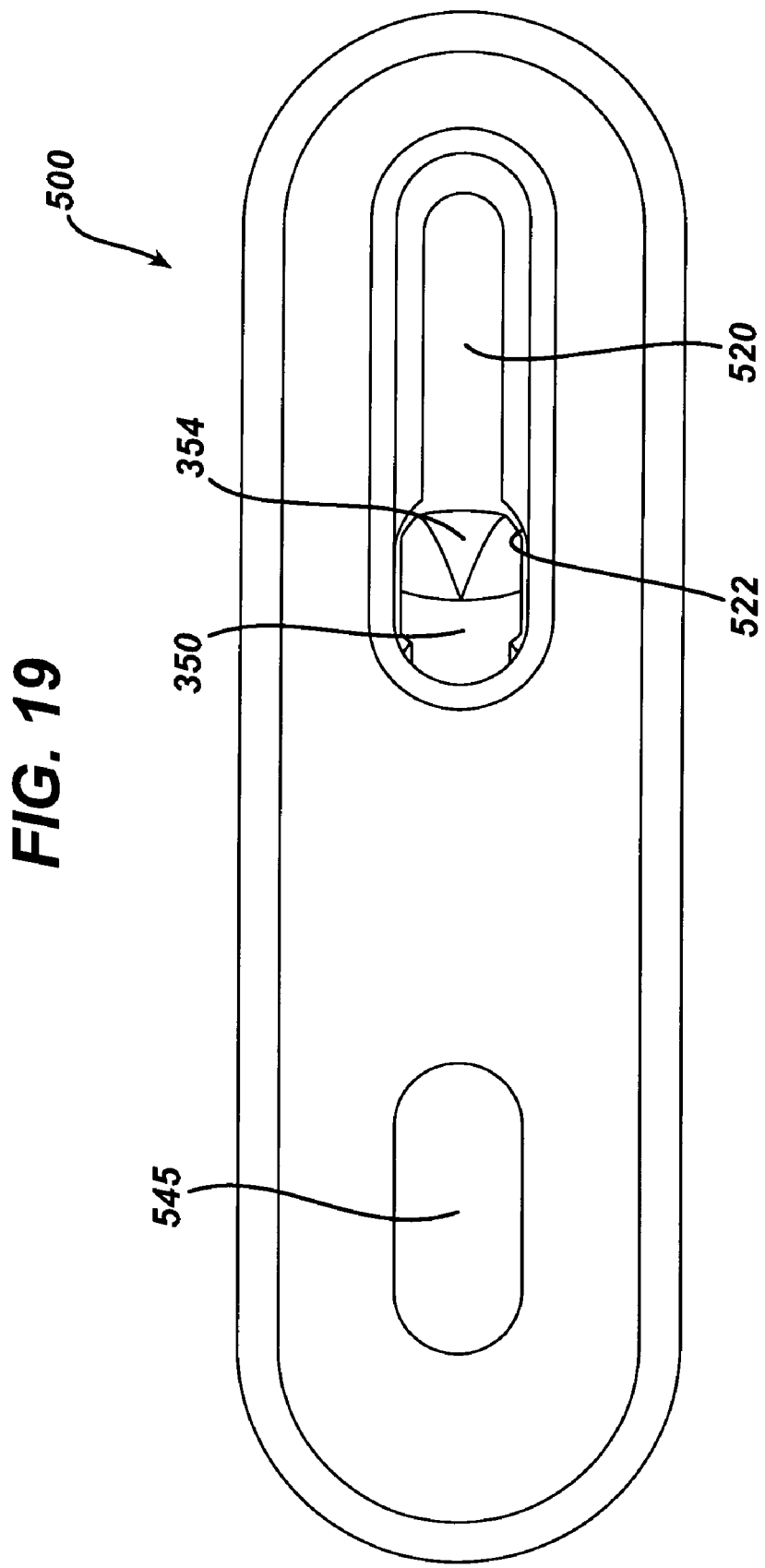
FIG. 19 illustrates the cartridge of FIG. 18 with the needle moved along the slot into the proximal opening.
Figure 20:
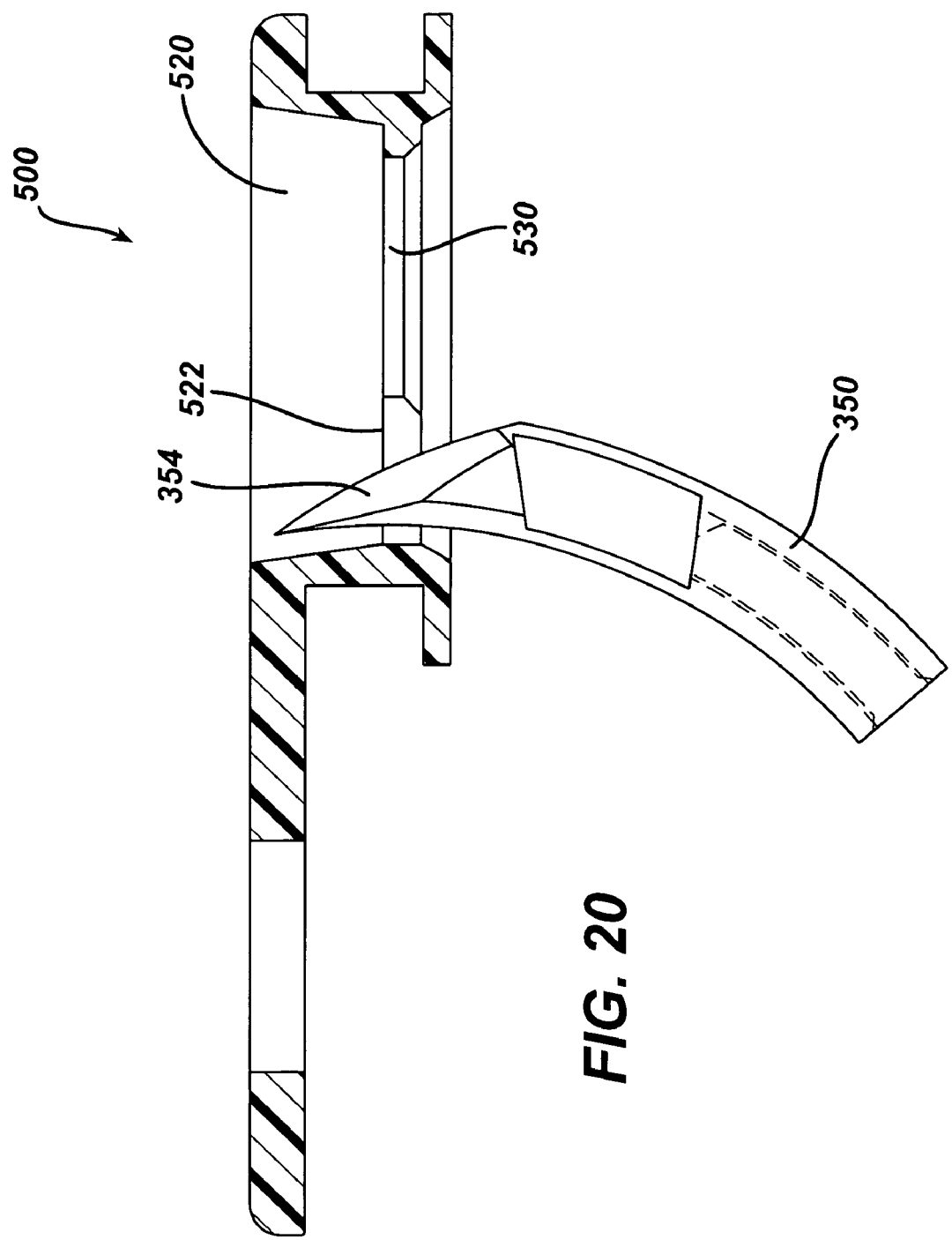
FIG. 20 is a cross-sectional view of the cartridge of FIG. 19 illustrating the needle in the proximal opening in position to be removed from the cartridge.

A patient is prepared for arthroscopic rotator cuff shoulder repair surgery in a conventional manner. The patient is anesthetized using conventional anesthesia and anesthesia procedures. The patient is positioned in a conventional manner to perform an arthroscopic Bankart procedure or to repair a torn rotator cuff. Bankart repair restores stability by re-attaching the labrum or capsule directly to the anterior glenoid cavity. Two anterior portal and tow posterior portals are then placed in a conventional manner using a conventional scalpel and conventional cannulas and blunt obturators. A conventional arthroscope is inserted into a cannula and the shoulder is insufflated in a conventional manner with sterile saline to provide the surgeon with a visible field and a view of the surgical site. After examining the site arthroscopically, the instrument of the present invention is armed with a surgical needle and suture and inserted into a cannula and positioned proximate to the surgical site. The detached inferior ligament labral complex is engaged in the jaws of the instrument as seen in FIG. 15, and the needle and suture are passed through the tissue such that the needle is engaged in the cavity of the cartridge. The tissue is disengaged from the jaws and the instrument is pulled out through the cannula where the suture is cut away from the needle that is engaged in the cartridge. The procedure is then completed in a conventional manner using conventional suture anchors implanted in the glenoid rim with the suture that has been passed through the labral complex to anchor the tissue to the glenoid rim. The wounds for the portals are then dosed in a conventional manner after removal of the cannulas and the procedure is complete.

Although this invention has been shown and described with respect to detailed embodiments thereof, it will be understood by those skilled in the art that various changes in form and detail thereof may be made without departing from the spirit and scope of the claimed invention.

We claim:

1. A suture passer instrument, comprising:
    a frame having a proximal end and a distal end, said frame having a longitudinal passage;
    a bottom jaw member mounted to the distal end of the frame, the bottom jaw having a passage for receiving a surgical needle;
    a top jaw member pivotally mounted to the distal end of the frame such that the top jaw member is moveable with respect to the bottom jaw member, said top jaw member having a distal opening for receiving a cartridge member;
    a handle member mounted to the proximal end of the frame, the handle member having a cavity;
    a jaw actuation member having a top end and a bottom end, wherein the top end of the jaw actuation member is mounted to the handle member;
    a needle rod driving trigger member having a top and a bottom, wherein the top of the needle rod driving member is pivotally mounted to the handle member;
    a jaw actuation rod having a proximal end a distal end, wherein the jaw actuation rod is slidably mounted in the passage of the frame and wherein the proximal end of the jaw actuation rod engages the top jaw member, and the proximal end of the actuation rod is mounted to the jaw actuation member;
    a needle driving rod slidably mounted to the frame, wherein the needle driving member has a proximal end mounted to the needle driving trigger and a distal end for engaging a needle;
    a needle passage in the lower jaw having a distal opening out through the top of the lower jaw and a proximal opening in communication with the longitudinal passage of the frame; and
    a cartridge member mounted to the top jaw, wherein the cartridge has an opening for receiving at least part of a surgical needle, said cartridge comprising:
    a member having a top, a bottom and a cavity extending therethough;
    a top flange mounted to the cartridge having an opening in communication with the cavity;
    a bottom flange mounted to the bottom of the member having an opening in communication with the cavity; and,
    at least one needle engagement tab member extending into the cavity.

2. The instrument of claim 1 additionally comprising a surgical needle mounted in the needle passage of the bottom jaw.

3. The instrument of claim 1 additionally containing an opening in the bottom jaw in communication with the needle passage.

4. The instrument of claim 1 wherein the cavity comprises a distal slot and a proximal opening, and wherein the tab member extends into the slot but does not extend into the proximal opening.

5. A suture passer instrument, comprising:
    a frame having a proximal end and a distal end, said frame having a longitudinal passage;
    a bottom jaw member mounted to the distal end of the frame, the bottom jaw having a passage for receiving a surgical needle;
    a top jaw member pivotally mounted to the distal end of the frame such that the top jaw member is moveable with respect to the bottom jaw member, said top jaw member having a distal opening for receiving a cartridge member;
    a handle member mounted to the proximal end of the frame, the handle member having a cavity;
    a jaw actuation member having a top end and a bottom end, wherein the top end of the jaw actuation member is mounted to the handle member;
    a needle rod driving trigger member having a top and a bottom, wherein the top of the needle rod driving member is pivotally mounted to the handle member;
    a jaw actuation rod having a proximal end a distal end, wherein the jaw actuation rod is slidably mounted in the passage of the frame and wherein the proximal end of the jaw actuation rod engages the top jaw member, and the proximal end of the actuation rod is mounted to the jaw actuation member;
    a needle driving rod slidably mounted to the frame, wherein the needle driving member has a proximal end mounted to the needle driving trigger and a distal end for engaging a needle;
    a needle passage in the lower jaw having a distal opening out through the top of the lower jaw and a proximal opening in communication with the longitudinal passage of the frame; and,
    a cartridge member removably mounted to the top jaw, said cartridge having an opening for receiving at least part of a surgical needle, wherein said cartridge comprises:
    a member having a top, a bottom and a cavity extending therethough;
    a top flange mounted to the cartridge having an opening in communication with the cavity;
    a bottom flange mounted to the bottom of the member having an opening in communication with the cavity; and,
    at least one needle engagement tab member extending into the cavity.

6. The instrument of claim 5 additionally comprising a surgical needle mounted in the needle passage of the bottom jaw.

7. The instrument of claim 5 additionally containing an opening in the bottom jaw in communication with the needle passage.

8. The instrument of claim 5 wherein the cavity comprises a distal slot and a proximal opening, and wherein the tab member extends into the slot but does not extend into the proximal opening.

9. A method of passing suture through tissue, the method comprising:
  I. providing a suture passer instrument, said instrument comprising:
    a frame having a proximal end and a distal end, said frame having a longitudinal passage;
    a bottom jaw member mounted to the distal end of the frame, the bottom jaw having a passage for receiving a surgical needle;
    a top jaw member pivotally mounted to the distal end of the frame such that the top jaw member is moveable with respect to the bottom jaw member, said top jaw member having a distal opening for receiving a cartridge member;
    a handle member mounted to the proximal end of the frame, the handle member having a cavity;
    a jaw actuation member having a top end and a bottom end, wherein the top end of the jaw actuation member is mounted to the handle member;
    a needle rod driving trigger member having a top and a bottom, wherein the top of the needle rod driving member is pivotally mounted to the handle member;
    a jaw actuation rod having a proximal end a distal end, wherein the jaw actuation rod is slidably mounted in the passage of the frame and wherein the proximal end of the jaw actuation rod engages the top jaw member, and the proximal end of the actuation rod is mounted to the jaw actuation member;
    a needle driving rod slidably mounted to the frame, wherein the needle driving member has a proximal end mounted to the needle driving trigger and a distal end for engaging a needle; and,
    a needle passage in the lower jaw having a distal opening out through the top of the lower jaw and a proximal opening in communication with the longitudinal passage of the frame;
  II. providing a cartridge member, said cartridge member comprising:
    a member having a top, a bottom and a cavity extending therethough;
    a top flange mounted to the cartridge having an opening in communication with the cavity;
    a bottom flange mounted to the bottom of the member having an opening in communication with the cavity; and,
    at least one needle engagement tab member extending into the cavity;
  III. providing a surgical needle having a distal piercing point and a proximal suture mounting end, said needle having a suture mounted to the suture mounting end;
  IV. mounting the cartridge member to the top jaw member;
  V. mounting the surgical needle in the needle passage of the bottom jaw member;
  VI. engaging tissue between the top jaw member and the bottom jaw member; and,
  VII moving the surgical needle and attached suture through the tissue by engaging the needle with the needle driving rod such that the needle is engaged in the cavity of the cartridge member.

10. The method of claim 9 additionally comprising the steps of opening the jaws with respect to each other, moving the instrument away from the tissue, and cutting the engaged needle from the cartridge member.

* * * * *